(12) United States Patent
Boyd et al.

(10) Patent No.: US 10,301,304 B2
(45) Date of Patent: May 28, 2019

(54) SELECTIVE INHIBITOR OF PHOSPHATIDYLINOSITOL 3-KINASE-GAMMA (71) Applicant: VERTEX PHARMACEUTICALS INCORPORATED, Boston, MA (US)

(72) Inventors: Michael John Boyd, Winchester, MA (US); Alex Aronov, Newton, MA (US); Hardwin O'Dowd, Boston, MA (US); Jeremy Green, Waltham, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 15/024,698

(22) PCT Filed: Sep. 25, 2014

(86) PCT No.: PCT/US2014/057499
§ 371 (c)(1),
(2) Date: Mar. 24, 2016

(87) PCT Pub. No.: WO2015/048318
PCT Pub. Date: Apr. 2, 2015

(65) Prior Publication Data
US 2016/0214980 A1 Jul. 28, 2016

Related U.S. Application Data (60) Provisional application No. 61/882,473, filed on Sep. 25, 2013.

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS 8,466,288 B2 * 6/2013 Aronov ................ C07D 401/04
435/184

FOREIGN PATENT DOCUMENTS

RU         2517194 C2    5/2014
WO    WO 2011/087776 A1 7/2011

OTHER PUBLICATIONS

Foster et al. 2012, Pharmacol. Rev. vol. 64, pp. 1027-1054.*
Ball et al. Aug. 2014, vol. 19, Issue 8, pp. 1195-1199.*
Patani et al. Chem. Rev. 1996, 96, pp. 3147-3176.*
International Search Report for PCT/US2014/057499, dated Feb. 12, 2014.
Written Opinion of the International Searching Authority for PCT/US2014/057499, dated Feb. 12, 2014.
Berge, J., et al., Pharmaceutical Salts, Pharmaceutical Sciences, 66:1-19, 1977.
Remington, The Science and practice of pharmacy, 21 Ed., Lippincott Williams and Wilkins, Philadelphia, PA.
CN Office Action and Notification to Grant Patent Right for Invention (transtated) for Application 201480060785.
SG Supplementary Examination Report and Notice of Eligibility for Grant (translated) for Application 11201602265P.
AU Examination Report for Application 2014324873.
JP Written Statement and Decision to Grant a Patent (translated) for Application 2016516904.
EP Communication for the Examining Division and Decision to Grant A European Patent for Application 14789651.8.
RU Office Action (translated) for Application 2016115726.
RU Application No. 2016115726 Decision to Grant (translated) dated Sep. 28, 2018.

* cited by examiner

*Primary Examiner* — Kara R McMillian
(74) *Attorney, Agent, or Firm* — Bryan Cave Leighton Paisner LLP (57) ABSTRACT

The present invention relates to a compound useful as a selective inhibitor of PI3Kγ. The invention also provides pharmaceutically acceptable compositions comprising said compounds and methods of using the compositions in the treatment of various disease, conditions, or disorders.

7 Claims, 4 Drawing Sheets

SELECTIVE INHIBITOR OF PHOSPHATIDYLINOSITOL 3-KINASE-GAMMA

CROSS-REFERENCE TO RELATED APPLICATIONS

The present application is the National Stage of International Application No. PCT/US2014/057499, filed on Sep. 25, 2014, which claims benefit to U.S. provisional application Ser. No. 61/882,473, filed Sep. 25, 2013. The entire contents of the above applications are incorporated by reference as if recited in full herein.

TECHNICAL FIELD OF THE INVENTION

The present invention relates to a compound useful as an inhibitor of the gamma isoform of phosphatidylinositol 3-kinase (PI3Kγ). The invention also provides pharmaceutically acceptable compositions comprising the compound of the invention and methods of using the compound and compositions in the treatment of various disorders.

BACKGROUND OF THE INVENTION

PI3Ks are a family of lipid kinases that catalyze the phosphorylation of the membrane lipid phosphatidylinositol (PI) on the 3'-OH of the inositol ring to produce PI 3-phosphate [PI(3)P, PIP], PI 3,4-bisphosphate [PI(3,4)P$_2$, PIP2] and PI 3,4,5-triphosphate [PI(3,4,5)P$_3$, PIP3]. PI(3,4)P$_2$ and PI(3,4,5)P$_3$ act as recruitment sites for various intracellular signaling proteins, which in turn form signaling complexes to relay extracellular signals to the cytoplasmic face of the plasma membrane.

Eight mammalian PI3Ks have been identified so far, including four class I PI3Ks. Class Ia includes PI3Kα, PI3Kβ and PI3Kδ. All of the class Ia enzymes are heterodimeric complexes comprising a catalytic subunit (p110α, p110β or p110δ) associated with an SH2 domain-containing p85 adapter subunit. Class Ia PI3Ks are activated through tyrosine kinase signaling and are involved in cell proliferation and survival. PI3Kα and PI3Kβ have also been implicated in tumorigenesis in a variety of human cancers. Thus, pharmacological inhibitors of PI3Kα and PI3Kβ are useful for treating various types of cancer.

PI3Kγ, the only member of the Class Ib PI3Ks, consists of a catalytic subunit p110γ, which is associated with a p101 regulatory subunit. PI3Kγ is regulated by G protein-coupled receptors (GPCRs) via association with βγ subunits of heterotrimeric G proteins. PI3Kγ is expressed primarily in hematopoietic cells and cardiomyocytes and is involved in inflammation and mast cell function. Thus, pharmacological inhibitors of PI3Kγ are useful for treating a variety of inflammatory diseases, allergies and cardiovascular diseases.

Although a number of PI3K-gamma inhibitors have been developed, there is a need for additional compounds to inhibit PI3K-gamma for treating various disorders and diseases. Particularly desirable are those PI3K-gamma inhibitors with improved pharmacokinetic/pharmacodynamics behavior in vivo, such as, for example, those inhibitors which increase the exposure of the drug to the target tissue while minimizing nontarget effects. A greater exposure per unit dose decreases the off target exposure relative to the exposure at the target tissue. Often the dose limiting toxicities occur in organs involved in clearing the drug from the circulation or in the case of an orally administered agent, in the gastrointestinal tract (GI). Decreased clearance and improved bioavailability increases the $C_{max}$ in the plasma while limiting the $C_{max}$ in the elimination organs such as kidney, liver, and GI. Further, increased absorption and decreased clearance (improved bioavailability) frequently results in less variability between patients in terms of exposure, thereby also improving the safety profile of the administered agent. In addition, agents that demonstrate improved physical properties, such as, for example, higher aqueous solubility, are also desirable.

SUMMARY OF THE INVENTION

It has been found that the compound of this invention, (R)-6-(1-(2,2-difluoroethyl)-1H-pyrazol-4-yl)-4,7,7-trimethyl-2-(5-(2,2,2-trifluoro-I-hydroxyethyl)pyridin3-yl)-6,7-dihydro-5H-pyrrolo[3,4-b]pyridin-5-one, and pharmaceutically acceptable compositions thereof, is an effective and selective inhibitor of PI3Kγ, with an improved pharmacokinetic/pharmacodyamic profile when compared to other PI3Kγ inhibitors. Accordingly, the invention features a compound having the following structure:

(Compound 1)

The invention also provides pharmaceutical compositions that include Compound 1 and a pharmaceutically acceptable carrier, adjuvant, or vehicle. These compounds and pharmaceutical compositions are useful for treating or lessening the severity of a variety of disorders, including inflammatory and immunoregulatory disorders, such as asthma, atopic dermatitis, rhinitis, allergic diseases, chronic obstructive pulmonary disease (COPD), septic shock, idiopathic pulmonary fibrosis, stroke, burn, joint diseases, rheumatoid arthritis, systemic lupus erythematosus, atherosclerosis, acute pancreatitis, psoriasis, inflammatory bowel disease (IBD), ulcerative colitis, Crohns' disease, and Graves' disease.

The compound and compositions provided by this invention are also useful for the study of PI3K in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

Compounds that have been drawn with stereochemical centers defined are stereochemically pure, but with the absolute stereochemistry still undefined. Such compounds can have either the R or S configuration. In those cases where such an absolute assignment has been determined, the chiral center(s) will be labeled R or S in the drawing. While Compound 1 herein is drawn in the R-configuration, the present invention includes embodiments in the S-configuration and in racemic mixtures of the R and S configurations.

The invention also features a pharmaceutical composition comprising any compound of the invention and a pharmaceutically acceptable carrier, adjuvant, or vehicle.

In one embodiment, the invention features a method of inhibiting PI3K kinase activity in a patient by administering to the patient Compound 1, or a pharmaceutical composition thereof. In a further embodiment PI3K-gamma is selectively inhibited over PI3K-alpha, PI3K-beta, or PI3K-delta.

In another embodiment, the invention features a method of treating or lessening the severity of a disease or condition selected from inflammatory and immunoregulatory disorders, such as asthma, atopic dermatitis, rhinitis, allergic diseases, chronic obstructive pulmonary disease (COPD), septic shock, idiopathic pulmonary fibrosis, stroke, burn, joint diseases, rheumatoid arthritis, systemic lupus erythematosus, atherosclerosis, acute pancreatitis, psoriasis, inflammatory bowel disease, ulcerative colitis, Crohns' disease, and Graves' disease in a patient by administering to the patient Compound 1, or a pharmaceutical composition thereof.

The invention also features a non-therapeutic method of inhibiting PI3K-gamma kinase activity in a biological sample in vitro comprising contacting said biological sample with Compound 1, or a composition containing said compound.

Compositions, Formulations, and Administration of Compounds of the Invention

In another aspect, the invention provides a pharmaceutical composition comprising Compound 1. For example, the invention provides a composition comprising Compound 1 or a pharmaceutically acceptable derivative thereof and a pharmaceutically acceptable carrier, adjuvant, or vehicle. In one embodiment, the amount of compound in a composition of this invention is such that it is effective to measurably inhibit PI3Kγ in a biological sample or in a patient. In one embodiment, the composition of this invention is formulated for administration to a patient in need of such composition. In a further embodiment, the composition of this invention is formulated for oral administration to a patient. The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, the compound as otherwise described herein, or a metabolite or residue thereof. As used herein, the term "inhibitory active metabolite or residue thereof" means that a metabolite or residue thereof is also an inhibitor of PI3K-gamma.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, C$_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues. The compounds of the present invention may be incorporated into other conventional sustained release formulations to provide for controlled release thereof over a desired time period, from hours to days to months.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of the compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg, such as 0.1-100 mg/kg and 0.1-10 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

In one aspect of the invention, the invention features a method of treating or lessening the severity of a PI3K-gamma-mediated condition or disease. The term "PI3K-gamma-mediated disease", as used herein means any disease or other deleterious condition in which the PI3K-gamma isoform is known to play a role.

Accordingly, in a further embodiment, the compound of the invention is selective for the inhibition of the PI3Kγ-isoform. In one embodiment, a compound or composition of the invention is selective for the inhibition of the PI3K gamma isoform over the PI3K alpha isoform in an in vitro assay by at least 20-fold. In another embodiment, the PI3Kγ-selective compound of the invention inhibits the gamma isoform over each of the alpha, beta, and delta isoforms in an in vitro assay by at least 20-fold. The present invention further includes using the selectivity of the compounds and compositions of the present invention in vivo to treat patients in need of such therapy.

The compound or compositions of the invention may be administered with one or more additional therapeutic agents, wherein the additional therapeutic agent is appropriate for the disease being treated and the additional therapeutic agent is administered together with the compound or composition of the invention as a single dosage form or separately from the compound or composition as part of a multiple dosage form. The additional therapeutic agent may be administered at the same time as the compound of the invention or at a different time. In the latter case, administration may be staggered by, for example, 6 hours, 12 hours, 1 day, 2 days, 3 days, 1 week, 2 weeks, 3 weeks, 1 month, or 2 months.

The invention provides a method of inhibiting PI3K-gamma kinase activity in a biological sample that includes contacting the biological sample with the compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly PI3K-gamma kinase activity, in a biological sample is useful for a variety of purposes known to one of skill in the art. Examples of such purposes include, but are not limited to, biological specimen storage and biological assays. In one embodiment, the method of inhibiting PI3K-gamma kinase activity in a biological sample is limited to non-therapeutic methods.

Preparation of the Compound of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

ATP adenosine triphosphate
Brine a saturated NaCl solution in water
CRED carbonyl reductase
DCM dichloromethane
DIEA diisopropylethylamine
DMA dimethylacetamide
DMAP 4-dimethylaminopyridine
DMF dimethylformamide
DMSO dimethylsulfoxide
dppfPdCl$_2$ 1,1'-bis(diphenylphosphino)-ferrocene dichloropalladium
DTT dithiothreitol
ESMS electrospray mass spectrometry
Et$_2$O ethyl ether
EtOAc ethyl acetate
EtOH ethyl alcohol
HEPES 4-(2-hydroxyethyl)-1-piperazineethanesulfonic acid
HPLC high performance liquid chromatography
LC-MS liquid chromatography-mass spectrometry
mCPBA meta-chloroperbenzoic acid
Me methyl
MeOH methanol
MTBE methyl t-butyl ether
MC methyl cellulose
NAD nicotinamide adenine dinucleotide
NMP N-methylpyrrolidine
Ph phenyl
RT or rt room temperature (between 20° C. and 25° C.)
tBu tertiary butyl
TBME tert-butyl methyl ether
TCA trichloroacetic acid
THF tetrahydrofuran
TEA triethylamine Synthetic Procedure

In general, Compound 1 may be prepared by methods described herein or by other methods known to those skilled in the art.

Example 1. Preparation of 2-chloro-6-(1-(2,2-difluoroethyl)-1H-pyrazol-4-yl)-4,7,7-trimethyl-6,7-dihydro-5H-pyrrolo[3,4-b]pyridin-5-one (Compound [1006])

Scheme 1

[1001]

As shown in step 1-iii of Scheme 1, a solution of 2-(chloromethyl)-3-(ethoxycarbonyl)-4-methylpyridine 1-oxide (Compound 1003, 69.3 g, 301.8 mmol) in phosphorus oxychloride (450.1 mL, 4.8 mol) was stirred under an atmosphere of nitrogen and heated at 95° C. for 60 hours. The reaction mixture was cooled to room temperature and the phosphorus oxychloride was distilled off in vacuo. The resulting dark colored residue was dissolved in dichloromethane (100 mL) and poured onto ice (500 g) in a 1 L beaker. The resulting mixture was stirred for 10 minutes. The pH of the mixture was adjusted to slightly above 7 with aqueous saturated NaHCO$_3$ solution. The organic phase was separated and the aqueous phase was back extracted with additional dichloromethane. The combined organic phases were sequentially washed with brine, dried over Na$_2$SO$_4$, filtered, and concentrated in vacuo. The residue was passed through a plug of silica gel using EtOAc/hexanes (1:3) to afford 80% pure product (as indicated by $^1$H NMR analysis) after removal of the volatiles under reduced pressure. This material was further purified via medium pressure silica gel chromatography (10-25% EtOAc/hexanes, 330 g Teledyne ISCO column) to afford ethyl 6-chloro-2-(chloromethyl)-4-methylnicotinate (Compound 1004, 36.5 g): ESMS (M+H)= 248.04.

As shown in step 1-iv of Scheme 1, to a solution of 1-(2,2-difluoroethyl)pyrazol-4-amine (48.2 g, 327.5 mmol) in isopropanol (1.7 L) was added ethyl 6-chloro-2-(chloromethyl)-4-methylnicotinate (Compound 1004, 65.0 g, 262.0 mmol) followed by N,N-diisopropylethyl amine (45.6 mL, 262.0 mmol). The reaction mixture was heated at 55° C. for 72 hours. The resulting thick white suspension was cooled to room temperature, filtered, and washed with additional isopropanol (200 mL) and diethyl ether (500 mL). The resulting solid was dried at 50° C. overnight in a vacuum oven to provide 56 g of 2-chloro-6-(1-(2,2-difluoroethyl)-1H-pyrazol-4-yl)-4-methyl-6,7-dihydro-5H-pyrrolo[3,4-b]pyridin-5-one (Compound 1005): $^1$H NMR (300 MHz, DMSO-d6) δ 8.28 (s, 1H), 7.87 (d, J=0.5 Hz, 1H), 7.52 (s, 1H), 6.37 (tt, J=54.9, 3.7 Hz, 1H), 4.85 (s, 2H), 4.67 (td, J=15.2, 3.7 Hz, 2H), 2.65 (s, 3H). This material contained 7% of the un-cyclized by-product [ethyl 6-chloro-2-(((1-(2,2-difluoroethyl)-1H-pyrazol-4-yl)amino)methyl)-4-methylnicotinate] and was used as is in subsequent reactions.

As shown in step 1-v of Scheme 1, to a solution of 2-chloro-6-(1-(2,2-difluoroethyl)-1H-pyrazol-4-yl)-4-methyl-6,7-dihydro-5H-pyrrolo[3,4-b]pyridin-5-one (Compound 1005, 46.0 g, 147.1 mmol) in DMF (782.0 mL) was added methyl iodide (20.1 mL, 323.6 mmol). The mixture was cooled to 5° C. and sodium hydride (12.9 g, 323.6 mmol of 60% dispersion in mineral oil) was added portionwise over 15 minutes. The reaction mixture was stirred at 3° C. for 45 minutes. HPLC analysis showed a mixture of monomethylation (10%), bis-methylation (74%), and tri-methylation (15%) products along with consumption of starting material. Additional sodium hydride (1.29 g, 32.36 mmol of 60% dispersion in mineral oil) was added and after an additional hour, HPLC analysis showed 84% bis-methylation desired product and 16% tri-methylated by-product. The reaction was quenched by the addition of aqueous saturated NH$_4$Cl (1 L), sodium thiosulfate (400 mL), and water (1 L). The aqueous phase was extracted twice with EtOAc (800 mL). The combined organic phases were dried (Na$_2$SO$_4$), filtered, and concentrated in vacuo. The residue was purified via medium pressure silica gel chromatography (0-40% EtOAc/hexanes gradient using a 800 g Teledyne ISCO column) to afford 2-chloro-6-(1-(2,2-difluoroethyl)-

As shown in step 1-i of Scheme 1, to a solution of ethyl 2,4-dimethylpyridine-3-carboxylate (Compound 1001, 20.2 g, 112.5 mmol) in dichloromethane (100 mL) under an atmosphere of nitrogen was added portionwise 1,3,5-trichloro-1,3,5-triazinane-2,4,6-trione (31.4 g, 135.0 mmol) over 15 minutes. The reaction mixture was stirred at room temperature for 18 hours. The resulting white precipitate was filtered and the filtrate was then washed sequentially with aqueous saturated NaHCO$_3$ solution (2×100 mL) and brine (100 mL). The organic phase was dried (Na$_2$SO$_4$), filtered, and concentrated in vacuo to afford ethyl 2-(chloromethyl)-4-methylnicotinate (22.9 g, Compound 1002) as a yellow oil: ESMS (M+H)=213.96. This material was used in the next step without further purification.

As shown in step 1-ii of Scheme 1, to a solution of ethyl 2-(chloromethyl)-4-methylnicotinate, (Compound 1002, 112.0 g, 524.2 mmol) in dichloromethane (484 mL) was added 3-chloroperoxybenzoic acid (141.0 g, 629.0 mmol). The reaction mixture was stirred under an atmosphere of nitrogen at room temperature overnight. The mixture was diluted with dichloromethane (200 mL) and washed sequentially with aqueous saturated NaHCO$_3$ (100 mL), aqueous saturated Na$_2$CO$_3$ (100 mL of 2M solution), and brine. The organic phase was dried (Na$_2$SO$_4$), filtered, and concentrated in vacuo to afford 2-(chloromethyl)-3-(ethoxycarbonyl)-4-methylpyridine-1-oxide (Compound 1003): ESMS (M+H)=230.25. This material was used in the next step without further purification:

1H-pyrazol-4-yl)-4,7,7-trimethyl-6,7-dihydro-5H-pyrrolo[3,4-b]pyridin-5-one (Compound 1006, 24 g) as a white solid: ¹H NMR (400 MHz, DMSO-d6) δ 8.21 (s, 1H), 7.83 (s, 1H), 7.54 (s, 1H) 6.58-6.25 (m, 1H), 4.67 (td, J=15.1, 3.7 Hz, 2H), 2.65 (s, 3H), 1.51 (s, 6H).

Example 2. Preparation of (R)-6-(1-(2,2-difluoroethyl)-1H-pyrazol-4-yl)-4,7,7-trimethyl-2-(5-(2,2,2-trifluoro-1-hydroxyethyl)pyridin-3-yl)-6,7-dihydro-5H-pyrrolo[3,4-b]pyridin-5-one (Compound 1)

analyzed by ¹H NMR in DMSO-d6 to monitor conversion of the starting material into product. After 1 hour 50% conversion was observed. After 3 hours >99% conversion was observed. The pH of the reaction was adjusted to 11 with 2M NaOH and stirred for 30 minutes in order to denature the enzyme. The pH was readjusted to 9 with 2M HCl. EtOAc (5 L) and diatomaceous earth (650 g) were added to the reaction mixture and stirring continued for 10 minutes. The resulting emulsion was filtered through a pad of diatomaceous earth to separate the organic and aqueous phases. The pad was washed with EtOAc (2 L) and the organic layer As shown in step 2-i of Scheme 2, water (10 L) was added to a 20 L reactor, followed by KH₂PO₄ (136 g). The mixture was stirred until homogeneity was achieved to provide a 0.1 M KH₂PO₄ buffer. The pH of this buffer was adjusted to pH 7.5 by the addition of 2M NaOH. The internal temperature was brought to 37° C. Approximately 500 mL of buffer was removed to be used for the later addition of NAD and CRED A131 cell paste (Almac Group, Ltd.). Accordingly, a solution of NAD (20 g) in buffer (100 mL) was added to the remaining 9.5 L of buffer, followed by a solution of 1-(5-bromopyridin-3-yl)-2,2,2-trifluoroethan-1-one (1020 g) in MTBE (1.5 L). Isopropanol (1 L) was used to rinse the addition flask into the reaction. The reduction was initiated by the addition of a suspension of CRED A131 cell paste (100 g) in buffer (400 mL) to the stirred reaction mixture. Over the course of the reaction, biphasic reaction samples (~2 mL) were taken from the stirring mixture, extracted using EtOAc (10 mL), dried over MgSO₄, evaporated, and separated. The aqueous layer was re-extracted with EtOAc (6 L) and the combined organic phases were washed with brine (4 L) and dried by adding MgSO₄ (200 g) and stirring for 30 minutes. Filtration and removal of the volatiles in vacuo afforded a pale yellow oil which rapidly solidified upon standing. The solid was broken up into chunks and slurried in cyclohexane (2 L). EtOAc (~500 mL) was added to the mixture which was stirred at 45° C. to dissolve the solids. The mixture was then re-concentrated in vacuo until a fine white solid started to precipitate from solution. Additional cyclohexane (2 L) was added and the solution cooled to 0° C. with an ice bath. After stirring for 30 minutes, the solids were collected by filtration, washed with cyclohexane (500 mL), and dried in a vacuum oven to afford 812 g of (R)-1-1-(5-bromopyridin-3-yl)-2,2,2-trifluoroethan-1-ol (Compound 1007, 99.95% ee by HPLC analysis) as a granular white solid: ¹H NMR (400 MHz, DMSO-d6) δ 8.72 (s, 1H), 8.61 (s, 1H), 8.08 (s, 1H), 5.09-5.15 (m, 1H).

As shown in step 2-ii of Scheme 2, a solution of (1R)-1-(5-bromo-3-pyridyl)-2,2,2-trifluoro-ethanol (Compound 1007, 49.5 g, 193.3 mmol), 4,4,5,5-tetramethyl-2-(4,4,5,5-tetramethyl-1,3,2-dioxaborolan-2-yl)-1,3,2-dioxaborolane (58.9 g, 232.0 mmol) and KOAc (37.9 g, 386.6 mmol) in dioxane (1.2 L) was flushed with nitrogen for 20 minutes. To the reaction mixture was added dppfPdCl$_2$*DCM (7.8 g, 9.7 mmol). The mixture was flushed with nitrogen for another 20 minutes and heated to reflux for 2 hours. After cooling to room temperature, the mixture was filtered through a pad of florisil (400 mL) and the cake was washed with 50% EtOAc/CH$_2$Cl$_2$ (1.5 L). The resulting filtrate was concentrated under reduced pressure to afford a yellow oil which was diluted with hexanes (800 mL) and concentrated in vacuo to afford a foamy yellow solid. Stirring the yellow solid with hexanes (800 mL) for 2 hours resulted in a white solid precipitate. The white solid was collected by filtration and dried to afford (1R)-2,2,2-trifluoro-1-[5-(4,4,5,5-tetramethyl-1,3,2-dioxaborolan-2-yl)-3-pyridyl]ethanol (Compound 1008, 48.4 g): $^1$H NMR (400 MHz, CDCl$_3$) δ 8.97 (s, 1H), 8.78 (s, 1H), 8.29 (s, 1H), 5.10-5.21 (m, 1H); 1.38 (s, 6H), 1.29 (s, 6H).

As shown in step 2-iii of Scheme 2, a solution of 2-chloro-6-(1-(2,2-difluoroethyl)-1H-pyrazol-4-yl)-4,7,7-trimethyl-6,7-dihydro-5H-pyrrolo[3,4-b]pyridin-5-one, (Compound 1006, 42.0 g, 123.3 mmol), (1R)-2,2,2-trifluoro-1-[5-(4,4,5,5-tetramethyl-1,3,2-dioxaborolan-2-yl)-3-pyridyl] ethanol (Compound 1008, 46.7 g, 148.0 mmol), and Na$_2$CO$_3$ (28.8 g, 271.3 mmol) in DMF (630 mL) and water (210 mL) was flushed with nitrogen for 30 minutes. To the mixture was added dppfPdCl$_2$*DCM (2.99 g, 3.699 mmol) and the mixture was flushed with nitrogen for another 30 minutes. The reaction mixture was heated to 103° C. and stirred for 2 hours. The mixture was cooled to room temperature and diluted with water (2 L). The aqueous phase was extracted twice with EtOAc (1 L). The combined organic phases were concentrated in vacuo under high vacuum to remove DMF. The residue was diluted with EtOAc and washed with water followed by washing with brine. The organic phase was dried (Na$_2$SO$_4$), filtered, and concentrated in vacuo. The crude residue was purified via medium pressure silica gel chromatography (0-100% EtOAc/hexanes gradient using a 1500 g Teledyne ISCO column) to afford 54 g of the desired product as a light red foamy solid. The solid was dissolved in dichloromethane, pushed through a florisil plug (200 mL) which was washed successively with EtOAc/CH$_2$Cl$_2$ mixtures [first 40% (1 L), then 60% (1 L), and then 80% (1 L)]. The filtrates were combined and concentrated in vacuo. The residue was twice diluted with heptanes (400 mL) and concentrated in vacuo to afford a cake, which was then washed with TBME to remove the light yellow color and dried in a vacuum oven at 60° C. for 4 days to afford (R)-6-(1-(2,2-difluoroethyl)-1H-pyrazol-4-yl)-4,7,7-trimethyl-2-(5-(2,2,2-trifluoro-1-hydroxyethyl)pyridin-3-yl)-6,7-dihydro-5H-pyrrolo[3,4-b]pyridin-5-one (Compound 1, 47 g): $^1$H NMR (400 MHz, CDCl$_3$) δ 9.33 (s, 1H), 8.75 (s, 1H), 8.54 (s, 1H), 8.01 (s, 1H), 7.75 (s, 1H), 7.62 (s, 1H), 6.14 (tt, J=55.4, 3.6 Hz, 1H), 5.28-5.11 (m, 1H), 4.51 (td, J=13.5, 4.2 Hz, 2H), 4.33 (d, J=4.6 Hz, 1H), 2.82 (s, 3H), 1.68 (s, 6H).

In Vitro Potency Against PI3K-Gamma Lipid Kinase

Example 3. PI3K Inhibition Assay

Using a Biomek FX from Beckman Coulter, 1.5 μL of each of ten 2.5-fold serial dilutions of the compound of the invention in 100% DMSO was added to an individual well (hereafter, "test well") in a 96 well polystyrene plate [Corning, Costar Item No. 3697]. One test well also contained 1.5 μL of DMSO with no compound. Another well contained an inhibitor in DMSO at a concentration known to completely inhibit the enzyme, (hereafter "background well"). Using a Titertek Multidrop, 50 μL of Reaction Mix [100 mM HEPES pH 7.5, 50 mM NaCl, 10 mM DTT, 0.2 mg/mL BSA, 60 μM phosphatidylinositol(4,5)-bisphosphate diC16 (PI(4,5)P$_2$; Avanti Polar Lipids, Cat. No. 840046P) and PI3K isoform of interest (see Table 1 for isoform concentrations)] was added to each well. To initiate the reaction, 50 μL of ATP Mix [20 mM MgCl$_2$, 6 μM ATP (100 μCi/μmole $^{33}$P-ATP was added to each well, followed by incubating the wells for 30 min. at 25° C. Final concentrations in each well were 50 mM HEPES 7.5, 10 mM MgCl$_2$, 25 mM NaCl, 5 mM DTT, 0.1 mg/mL BSA, 30 μM PI(4,5)P$_2$, 3 μM ATP, and the PI3K isoform of interest (see Table 2). Final compound concentrations in each well ranged from 10 μM to 1 nM.

TABLE 1

|  | PI3K Isoform Concentrations | | | |
| --- | --- | --- | --- | --- |
|  | PI3K-α | PI3K-β | PI3K-γ | PI3K-δ |
| Enzyme concentration in Reaction Mix | 4 nM | 20 nM | 4 nM | 4 nM |
| Final enzyme concentration | 2 nM | 10 nM | 2 nM | 2 nM |

After incubation, the reactions in each well were quenched by addition of 50 μL of stop solution [30% TCA/Water, 10 mM ATP]. Each quenched reaction mixture was then transferred to a 96 well glass fiber filter plate [Corning, Costar Item No. 3511]. The plate was vacuum-filtered and washed three times with 150 μL of 5% TCA/water in a modified Bio-Tek Instruments ELX-405 Auto Plate Washer. 50 μL of scintillation fluid was added to each well and the plate read on a Perkin-Elmer TopCount™ NXT liquid scintillation counter to obtain $^{33}$P-counts representing inhibition values.

The value for the background well was subtracted from the value obtained for each test well and the data were fit to the competitive tight binding Ki equation described by Morrison and Stone, *Comments Mol. Cell Biophys.* 2: 347-368, 1985. The degree of PI3K-gamma inhibition for Compound 1 varied linearly with ATP concentration demonstrating competitive inhibition, with a Ki value of 8+/−4 nM. In addition, isoform selectivity was also seen as Compound 1 was tested against PI3K-alpha, PI3K-beta, and PI3K-delta isoforms and was determined to have a selectivity of greater than 15 fold for PI3K-gamma as shown in Table 2.

TABLE 2

| PI3K Isoform Selectivity for Compound 1 | | |
| --- | --- | --- |
| Isoform | Ki (μM) | Fold Selectivity |
| PI3Kα | 0.28 ± 0.09 | 30 |
| PI3Kβ | 0.22 ± 0.03 | 26 |
| PI3Kδ | 0.16 ± 0.05 | 19 |
| PI3Kγ | 0.008 ± 0.004 | NA |

Cellular Potency

PI3Ks are multisubunit complexes comprised of a regulatory subunit and a catalytic subunit. This class of enzymes catalyzes the phosphorylation of phosphatidylinositol-4,5-bisphosphate (PIP2) giving rise to second messenger phosphatidylinositol-3,4,5-triphosphate (PIP3). Activation of receptors leads to transient increase in PIP3 levels. PIP3 acts as a docking site at the plasma membrane, recruiting and activating the pleckstrin homology (PH) domain containing proteins, such as Akt, PDK-1, Tek kinases etc. These then regulate key cellular functions such as growth, metabolism, migration, respiratory burst etc. As the downstream effectors are common in the PI3K signaling pathway, it is the receptors that determine which isoform of PI3K is recruited upon activation. Based on this, a number of biochemical-pAkt based and functional assays were used to analyze potency and selectivity of PI3K-gamma inhibitors relative to the other PI3K isoforms.

Example 4. MCP-1 Stimulated pAkt in THP-1 Cells

Chemokines like MCP-1 bind to their receptors resulting in activation of the PI3K-gamma signaling pathway. PI3K-gamma leads to generation of PIP3 and activation of downstream molecules like PDK-1 and Akt. Akt phosphorylation is a measure of PI3K activity in the cell. In this assay, THP-1 cells (human monocytic cell line) are starved overnight to deplete pAkt levels. Subsequent stimulation with MCP-1 for 3 minutes leads to PI3K-gamma-induced phoshorylation of Akt at the Threonin 308 and Serine 473 sites. Cells were fixed and stained for intracellular phosphoAKT (Ser 473) then analyzed using a BD FACSCalibur™ cytometer resulting in a measure of cellular PI3K-gamma activity. Compound 1 had an $IC_{50}$ of 0.24±0.07 µM in this assay. See Table 3.

TABLE 3

Potency of Compound 1 in PI3Kα/β/δ dependent in-vitro assays

| Cell Assay | PI3K isoform dependency | IC50 (µM) Average ± Standard Deviation | Number of Assays (N) |
| --- | --- | --- | --- |
| THP-1/MCP-1/pAkt | PI3K-gamma | 0.24 ± 0.07 | 20 |
| Isolated Leukocyte oxidative burst | PI3K-gamma | 0.22 ± 0.08 | 3 |
| Whole Blood oxidative burst | PI3K-gamma | 0.57 ± 0.08 | 3 |

Example 5. Whole Blood and Leukocyte Oxidative Burst Assay

Neutrophils, monocytes and macrophages are key mediators of innate immunity. They release reactive oxygen species (ROS) as part of the innate immune inflammatory response. ROS production is induced by inflammatory mediators like chemokines, bacterial peptides and complement that recruit the innate immune cells to the site of inflammation. These inflammatory mediators trigger activation of PI3K-gamma and initiate a downstream signaling cascade that leads to the assembly of the complete NADPH oxidase complex at the plasma membrane generating ROS. PI3K-gamma functional activity was measured in whole blood and buffy coat neutrophils and monocytes via the generation of ROS. The cells are stimulated with TNF-alpha for 10 minutes, then with bacterial cell wall-derived chemotactic peptide, fMLP, for 20 minutes, and loaded with a non-fluorescent dye dihydrorhodamine 1,2,3 (DHR). ROS produced by the cells oxidizes DHR to fluorescent rhodamine causing an increase in fluorescent rhodamine content in the cells. PI3K-gamma functional activity is measured by the ability of neutrophils and monocytes to generate ROS following fMLP stimulation. Leukocytes and whole blood samples were analyzed on a BD FACSCalibur™ to quantitate cells positive for fluorescent rhodamine. Buffy coat cells generate $IC_{50S}$ in the absence of serum and whole blood assay generates $IC_{50S}$ in the presence of serum. Compound 1 had an $IC_{50}$ of 0.22 µM in the buffy coat leukocyte assay and 0.57 µM in the whole blood assay. See Table 3.

Example 6. CSF-1 Stimulated pAkt in THP-1 Cells

Growth factors, cytokines and other ligands of receptor tyrosine kinases, like CSF1, bind to their receptors leading to activation of the class IA PI3K signaling pathway. PI3K activation leads to generation of PIP3 and activation of downstream molecules like PDK-1 and Akt. Akt phosphorylation is a measure of PI3K activity in the cell. THP-1 cells (a human monocytic cell line) are starved overnight to deplete pAkt levels. Stimulation with CSF-1 for 5 minutes leads to PI3Kα/β/δ induced phoshorylation of Akt at the Threonine 308 and Serine 473 sites. Cells were fixed and stained for intracellular phosphoAkt (Ser 473) then analyzed on the BD FACSCalibur™ cytometer. This is a measure of cellular Class IA PI3K inhibition. Compound 1 had an $IC_{50}$ of >9.7 µM in this assay, demonstrating selectivity over the Class IA PI3Ks. See Table 4.

Example 7. Human B Cell Proliferation Assay

B cells are highly dependent on PI3Kδ for their development and activity. PI3K-gamma has an essential and non-redundant role in signaling via the B cell receptor (BCR) complex. Both IgM induced Ca+ influx and proliferation are attenuated in mice lacking PI3K-δ or with PI3K-δ inhibitors. PI3K-gamma has no role to play in any B cell activity. The specificity of the BCR complex for the PI3K-gamma isoform makes this an ideal PI3K-gamma assay to evaluate the extent of PI3K-gamma inhibition in cells. Purified human B cells are stimulated with anti-IgM in the presence of test compounds. Four days later cell viability/proliferation was measured using cell titer-glo to measure the ATP content of the cells in the well. Lack of or reduced proliferation is a measure of the extent of PI3K-gamma inhibition. Compound 1 has an $IC_{50}$ of 3.05±0.44 µM demonstrating a 11-fold selectivity window over PI3K-δ. See Table 4.

Example 8. HUVEC Proliferation Assay

PI3Ks are important signaling molecules downstream of a number of growth factors that regulate cell survival, growth and cell cycle entry. Both PI3K-alpha and PI3K-beta isoforms regulate cell cycle entry; inhibition of either isoform leads to reduced cell growth. HUVECs are primary human umbilical vein endothelial cells which express both the PI3Kα and PI3Kβ isoforms. Inhibition of either or both PI3K-alpha or PI3K-beta isoforms will inhibit the cell growth of HUVECs. Compounds are plated onto HUVECs, cell proliferation/viability is measure 96 hours post compound treatment using cell titer-glo to measure the ATP content of the cells in the well. Lack of or reduced proliferation is a measure of the extent of PI3K-alpha and/or PI3K-beta inhibition. Compound 1 had an $IC_{50}$ of >19 µM in this assay, demonstrating a selectivity of >74-fold over PI3K-alpha/beta. See Table 4.

Example 9. MCF-7 Proliferation Assay

The PI3K-Akt signaling pathway regulates many normal cellular processes including cell proliferation, survival and growth that are critical for tumorigenesis. Dysregulation of the PI3K signaling pathway occurs commonly in human cancers. MCF7 is a human breast carcinoma cell line that has an activating E545K PI3Kα heterozygous mutation in the helical domain of the p110α protein leading to hyperactivity of the PI3K-alpha pathway. Inhibition of PI3K-alpha signaling in the MCF7 cells inhibits cell growth and hence inhibitors of PI3K-alpha can be evaluated in the MCF7 proliferation assay. Compounds are added to MCF7 cells, cell proliferation/viability is measured 96 hours post compound treatment using cell titer-glo to measure the ATP content of the cells in the well. Lack of or reduced proliferation is a measure of the extent of PI3K-alpha inhibition. Compound 1 had an $IC_{50}$ of >17 µM in this assay, thus demonstrating a selectivity of >67-fold over PI3K-alpha. See Table 4.

As shown above, Compound 1 has excellent potency, 0.25 µM in PI3K-gamma associated cell assays, has a 12-fold selectivity over PI3K-delta, and 40-80 fold selectivity over PI3K-alpha and PI3K-beta in cell based assays.

TABLE 4

Potency of Compound 1 in PI3Kα/β/δ dependent in vitro assays

| Cell Assay | PI3K isoform dependency | IC50 (µM) Avg +/− SD | Number of Assays (N) |
|---|---|---|---|
| THP-I/CSF-1/pAkt | PI3K-alpha/beta/delta | >9.7 ± 0.7 | 20 |
| B cell/IgM/Proliferation | PI3K-gamma | 3.05 ± 0.44 | 5 |
| HUVEC Proliferation | PI3K-alpha/beta | >19 | 5 |
| MCF7 Proliferation. | PI3K-alpha | >17** | 4 |

*Individual assay data (µM) - >20, >20, 19.8
**Individual assay data (µM) - 15.7, >20, 18, 17

Drug Metabolism

Example 10. Metabolism of Compound 1 by Recombinant CYP Enzymes

Microsomes that contained recombinant CYP enzymes (CYP1A2, 2B6, 2C8, 2C9, 2C19, 2D6, 2E1 and 3A4) were used to determine which CYP catalyzes the oxidation of Compound 1. Accordingly, Compound 1 (1 µM) was incubated with individual recombinant CYPs in the presence of the cofactor NADPH. The percent parent drug remaining at the end of the incubation period was determined by LC-MS/MS and compared to that present at the beginning. Results are shown in Table 5. Metabolism of Compound 1 was detected only in the incubation with CYP3A4, albeit at a low apparent rate.

TABLE 5

Stability of Compound 1 in Incubations with Recombinant CYP Enzymes*

| CYP | 1A2 | 2B6 | 2C8 | 2C9 | 2C19 | 2D6 | 2E1 | 3A4 |
|---|---|---|---|---|---|---|---|---|
| % Parent Remaining @ 30 min | 105 | 107 | 105 | 108 | 118 | 100 | 105 | 92 |

*Data are expressed as Mean (SD)

Example 11. Inhibition of CYP Enzymes by Compound 1

The potential for Compound 1 (0.01 to 100 µM) to reversibly inhibit CYP enzymes (CYP1A2, 2B6, 2C8, 2C9, 2C19, 2D6 and 3A4) in human liver microsomes was evaluated. Inhibition assays were conducted with selective CYP probes for each CYP enzyme at specific concentrations of substrate (close to its dissociation constant (Km) value). Data are shown in Table 6. Compound 1 was a moderate inhibitor of CYP 1A2, 2B6 and 2C8; $IC_{50}$ values ranged from 4-7 µM.

TABLE 6

Inhibition by Compound 1 of CYP Enzymes in Human Liver Microsomes

| Substrate | Enzyme | $IC_{50}$ (µM) |
|---|---|---|
| 30 µM Phenacetin | CYP1A2 | 7 |
| 100 µM Bupropion | CYP2B6 | 4 |
| 2.5 µM Paclitaxel | CYP2C8 | 7 |
| 2.5 µM Diclofenac | CYP2C9 | 32 |
| 30 µM S-Mephenytoin | CYP2C19 | 21 |
| 10 µM Bufuralol | CYP2D6 | 64 |
| 50 µM Testosterone | CYP3A4 | >75 |
| 2.5 µM Midazolam | CYP3A4 | 19 |

Time-dependent inhibition of CYP3A4 by Compound 1 also was evaluated in human liver microsomes using the $IC_{50}$ shift assay. In the study, Compound 1 at 0.1 to 50 µM was preincubated with human liver microsomes in the presence and absence of NADPH for 0 and 30 minutes. Incubations were then diluted 10-fold with buffer and the remaining CYP3A4 (testosterone-6-beta-hydroxylase) activity was measured over a 10 minute period. There was no significant change ($IC_{50}$ shift=1) in the $IC_{50}$ of Compound 1 in the presence or absence of NADPH.

This result was verified in a follow-up study where CYP3A4 time-dependent inhibition in human liver microsomes was evaluated after preincubation with either 10 or 50 µM Compound 1 over a period of 0, 5, 10, 15 and 30 minutes. The observed rate constant for loss of CYP3A4 activity in the study (Kobs) was 0.0039/min at both concentrations tested as compared with Kobs=0.053/min for mifepristone, the positive control. The data from both of these studies demonstrate that Compound 1 does not inhibit CYP3A4 in a time-dependent manner.

Example 12. Enzyme Induction

The potential of Compound 1 to activate the pregnane-X receptor (PXR) was evaluated over a range of six concentrations from 0.1-30 µM in DPX2 cells, a human hepatoma cell line that is stably overexpressed with the human PXR gene and a luciferase reporter gene linked to two promoters in the human CYP3A4 gene. Rifampicin was used as a positive control. In that assay, Compound 1 showed an insignificant level of activation giving a response that was 5% that of the positive control with an EC50 value >30 µM.

The potential of Compound 1 to induce CYP1A2 and CYP3A4 also was valuated in hepatocytes. Compound 1 at concentrations of 0.1-30 µM was incubated with cultured cryopreserved primary human hepatocytes from three different donors for 48 hours and was compared to the effect of positive controls (i.e., CYP inducers: 50 µM Omeprazole for CYP1A2 and 10 µM rifampicin for CYP3A4). CYP activity was determined by monitoring metabolite formation of specific CYP probe substrates (phenacetin for CYP1A2 and testosterone for CYP3A4) using LC-MS/MS. CYP messenger ribonucleic acid (mRNA) was analyzed by RT-PCR to confirm CYP induction potential. Results are shown in Table 7.

The change in CYP1A2 or CYP3A4 activity and mRNA levels in all three hepatocyte lots after exposure to Compound 1 was less than 20% of the positive control. These in vitro data indicate that Compound 1 has a low potential to induce CYP1A2 or CYP3A4 after 48 hour exposure in human hepatocytes.

TABLE 7

CYP1A2 and CYP3A4 Induction by Compound 1 in Human Hepatocytes

| Treatment | CYP1A2 Induction Potential[a] Human Hepatocyte Lot # | | |
|---|---|---|---|
| | LMP | YOW | 8123 |
| | Phenacetin O-Dealkylation (mRNA message) | | |
| 50 µM Omeprazole | 36.3 (71.5) | 17.9 (83.6) | 25.7 (118.0) |
| 0.5 µM Compound 1 | 0.7 (0.6) | 1.1 (0.5) | 0.6 (0.6)* |
| 1.0 µM Compound 1 | 0.8 (0.6) | 1.1 (0.4) | 0.5 (0.5) |
| 5.0 µM Compound 1 | 0.9 (0.7) | 1.1 (0.6) | 0.8 (0.5) |
| 10.0 µM Compound 1 | 1.0 (0.8) | 1.2 (1.3) | 0.7 (1.2) |
| 20.0 µM Compound 1 | 1.1 (0.7) | 1.3 (0.8) | 1.2 (2.6) |
| 30.0 µM Compound 1 | 1.1 (1.4) | 1.5 (NR[2]) | 1.3 (NR[2]) |
| | CYP3A4 Induction Potential[a] Human Hepatocyte Lot # | | |
| Treatment | LMP | YOW | 8123 |
| | Testosterone-6β-Hydroxylation (mRNA message) | | |
| 10 µM Rifampicin | 13.2 (10.4) | 16.0 (29.3) | 40.4 (210.3) |
| 0.5 µM Compound 1 | 0.9 (1.0) | 1.0 (1.3) | 0.3 (0.4) |
| 1.0 µM Compound 1 | 0.8 (0.7) | 0.8 (0.2) | 0.5 (0.3) |
| 5.0 µM Compound 1 | 1.1 (1.1) | 0.9 (NR[1]) | 0.4 (0.5) |
| 10.0 µM Compound 1 | 1.1 (1.5)* | 0.8 (NR[1]) | 0.4 (1.1) |
| 20.0 µM Compound 1 | 1.4 (3.0) | 0.6 (NR[1]) | 0.6 (0.7) |
| 30.0 µM Compound 1 | 1.0 (2.5) | 0.6 (NR[1]) | 0.7 (NR[2]) |

[a]Expressed as fold change relative to solvent control
NR[1] not reported since response was less than vehicle control
NR[2] not reported due to cytotoxicity

Example 13. Permeability of Efflux Potential

The permeability of Compound 1 was evaluated using both Caco-2 and MadinDarby canine kidney (MDCK) wild-type cell lines. Cells were exposed to drug in buffer on the apical side (measuring permeability in the A-to-B direction) or basolateral side (measuring permeability in the B-to-A direction) and incubated at 37° C. for one hour. Results are shown in Table 7. Permeability was high in the A-to-B direction in both the MDCK and Caco-2 cell lines (33 and $18 \times 10^{-6}$ cm/sec, respectively).

An assessment of whether Compound 1 is a substrate of efflux transporters was conducted by using the MDCK cell line that is overexpressed with human P-gp (MDR). Vectorial transport was detected in this cell line (efflux ratio=35.1), indicating that Compound 1 is a P-gp substrate. See Table 8.

TABLE 8

Summary of Efflux Ratio and Recovery of Compound 1 in Caco-2, MDCK-WT and MDCK-MDR1 Cell Lines

| Cell Line | Compound 1 conc. | | Avg. $P_{app}$ ($\times 10^{-6}$ cm/sec) ± SD | Avg. % Recovery ± SD | Efflux Ratio |
|---|---|---|---|---|---|
| Caco-2 | 5 µM | A > B | 32.6 | 87 | 1.9 |
| | | B > A | 60.7 | 96 | |
| MDCK-WT | 1 µM | A > B | 17.55 | 90 | 1.4 |
| | | B > A | 23.78 | 93 | |
| MDCK-MDR1 | 1 µM | A > B | 0.98 | 97 | 35.1 |
| | | B > A | 34.33 | 87 | |

In Vivo Pharmacokinetics

Example 14. Intravenous Bolus Dosing

Following intravenous administration of a single bolus dose, Compound 1 had low systemic clearance and a long half-life in all species tested. See Table 9. The clearance values of Compound 1 represent approximately 5.4%, 3.6%, 13% and 26% of hepatic blood flow in mouse, rat, dog and monkey. The volume of distribution was greater than the total body water, indicating distribution of Compound 1 to tissues.

TABLE 9

Mean Pharmacokinetic Parameters for Compound 1 Following Single IV Bolus Administration

| Species | Nominal Dose[b] (mg/kg) | $AUC_{ALL}$ (µg*hr/mL) | $AUC_{INF}$ (µg*hr/mL) | $DN\_AUC_{INF}$ (µg*hr/mL) | CL (mL/min/kg) | % $HBF^{a}$ | $T_{1/2}$ (hr) | $V_{ss}$ (L/kg) |
|---|---|---|---|---|---|---|---|---|
| Mouse | 0.45 | 1.09 | 1.53 | 3.4 | 4.9 | 5.4 | 4.3 | 1.8 |
| Rat | 0.5 | 2.69 | 3.1 | 6.2 | 2.8 | 3.6 | 8.2 | 1.8 |
| Dog | 0.5 | 1.9 | 2.0 | 4.0 | 5.4 | 13 | 10.7 | 3.9 |
| Monkey | 0.5 | 0.7 | 0.74 | 1.5 | 11.5 | 26 | 6.6 | 3.3 |

[a]HBF, hepatic blood flow
[b]Measured doses were 0.32, 0.47, 0.5 and 0.46 mg/kg for mouse, rat, and monkey, respectively. PK calculations were based on nominal dose.

Example 15. Oral Bioavailability

As shown in Table 10, the oral bioavailability of Compound 1 was high (>80%) following administration of a single dose of Compound 1 to mouse, rat, dog and monkey. The bioavailability in monkey (greater than 100%) may be explained by the tenfold difference between the IV and oral doses. Compound 1 was rapidly absorbed in all species, with maximum systemic concentration observed within approximately one to three hours of dosing.

TABLE 10

Mean Pharmacokinetic Parameters for Compound 1 Following Single Oral Administration to Mouse, Rat, Dog and Monkey

| Species | Nominal Dose[c] (mg/kg) | AUC$_{ALL}$ (µg*hr/mL) | AUC$_{INF}$ (µg*hr/mL) | DN_AUC$_{INF}$ (µg*hr/mL) | C$_{max}$ (µg/mL) | T$_{max}$ (hr) | T$_{1/2}$ (hr) | MRT (hr) | F % |
|---|---|---|---|---|---|---|---|---|---|
| Mouse[a] | 1 | 2.72 | 2.76 | 2.76 | 0.29 | 2 | 3.8 | 5.8 | 81 |
| Rat[b] | 1 | 5 | 5.11 | 5.14 | 0.26 | 3.33 | 12.5 | 18.3 | 84 |
| Dog[b] | 3* | 9.11 | 9.29 | 3.1 | 1.29 | 0.83 | 7.3 | 9 | 77 |
| Monkey[b] | 5 | 12.3 | 12.5 | 2.5 | 1.35 | 1.67 | 8.5 | 10.5 | 126 |

[a]Vehicle: 0.2% MC/1% SLS
[b]Spray-dried dispersion, vehicle: 2% TPGS/1.5% HPMCAS-HF/1.5% PVP-VA with 50 mM citrate pH 5
[c]Measured doses were 0.95, 0.68, 2.6 and 4.4 mg/kg for mouse, rat, and monkey, respectively. PK calculations were based on nominal dose.

Table 11 provides pharmacokinetic data for PI3K inhibitors described in International Patent Application Pub. No. WO 2011/087776 ("the '776 application"), each of which having the same core pharmacophore structure as that of Compound 1. See compounds 705, 709, 735, and 772 on pages 229, 229, 234, and 242, respectively, of the '776 application. The systemic plasma clearance of Compound 1 following intravenous delivery was significantly (2.5 times to 8 times) lower than observed in studies with other compounds. The plasma clearance data are in agreement with intravenous data, oral exposure, AUC, and C$_{max}$ values. These data show that Compound 1 has an unexpectedly favorable pharmacokinetic profile vs. these compounds.

TABLE 11

Mean Pharmacokinetic Parameters for Orally Administered Compound 1 vs. Comparator Compounds

| Compound Number | Structure | Rat IV[1] AUC (µg · hr/mL) | Rat IV CL (mL/min/kg) | Rat PO[2] AUC (µg · hr/mL) | Rat PO C$_{max}$ (µg/mL) |
|---|---|---|---|---|---|
| 1 | (structure) | 3.1 | 2.8 | 18 | 1.0 |
| A (No. 705 in WO 2011/087776) | (structure) | 0.22 | 22 | 0.3 | 0.06 |
| B (No. 709 in WO 2011/087776) | (structure) | 0.33 | 22 | 0.6 | 0.12 |
| C (No. 735 in WO 2011/087776) | (structure) | 0.59 | 11 | 3 | 0.2 |

TABLE 11-continued

Mean Pharmacokinetic Parameters for Orally Administered Compound 1 vs. Comparator Compounds

| Compound Number | Structure | Rat IV[1] AUC (µg · hr/mL) | Rat IV CL (mL/min/kg) | Rat PO[2] AUC (µg · hr/mL) | Rat PO $C_{max}$ (µg/mL) |
|---|---|---|---|---|---|
| D (No. 772 in WO 2011/087776) |  | 1.2 | 7 | 9 | 0.5 |

[1]Intravenous bolus study, 0.5 mg/kg nominal dose; Vehicle 355 PEG400/25%NMP/40%Water
[2]Oral gavage study, 3 mg/kg nominal dose; vehicle 0.2%MC/1%SLS

Example 16. Tissue Distribution in Rats

Compound 1 distributed well into most tissues after an oral dose of 5 mg/kg administered to male rats. See Table 12. The brain and cerebrospinal fluid (CSF) were the organs which showed very low exposure to Compound 1 with a $C_{max}$ of 111 ng/g and 27 ng/mL, respectively (<0.1% of the plasma exposure). Compound 1 distributed well to the liver and kidney, with a $C_{max}$ of 11400 and 4770 ng/g, respectively. The tissue to plasma ratio followed the trend of liver>kidney>heart>lung>spleen>brain>CSF. The elimination kinetics of Compound 1 in each examined organ followed plasma kinetics. There was no evidence for tissue accumulation of Compound 1 after a single dose administration.

TABLE 12

Mean Tissue and Plasma Concentrations and Tissue to Plasma Ratio of Compound 1 Following a Single 5 mg/kg Oral Dose

| Tissue | Compound 1 Concentration (ng/ml or ng/g) | | | | | Tissue to Plasma Ratio | | | | |
|---|---|---|---|---|---|---|---|---|---|---|
| Hr post dose | 0.5 | 2 | 7 | 24 | 48 | 0.5 | 2 | 7 | 24 | 48 |
| Brain | 74 | 129 | 111 | 30 | 9.35 | 0.04 | 0.07 | 0.05 | 0.06 | 0.07 |
| CSF | 20 | 23.3 | 27 | 5 | BQL | 0.01 | 0.01 | 0.01 | 0.01 | BQL |
| Heart | 1730 | 3280 | 3100 | 771 | 196 | 0.98 | 1.67 | 1.40 | 1.46 | 1.39 |
| Kidney | 3070 | 4980 | 4770 | 1600 | 673 | 1.75 | 2.54 | 2.16 | 3.03 | 4.76 |
| Liver | 8710 | 13700 | 11400 | 3010 | 750 | 4.96 | 6.99 | 5.13 | 5.69 | 5.32 |
| Lung | 2180 | 2710 | 2700 | 617 | 185 | 1.24 | 1.38 | 1.22 | 1.17 | 1.31 |
| Spleen | 1290 | 1790 | 491 | 125 | BQL | 0.74 | 1.15 | 0.81 | 0.93 | 0.88 |
| Plasma | 1760 | 1960 | 2210 | 592 | 141 | — | — | — | — | — |

BQL = Below the quantifiable limit. The compound was dosed as spray-dried dispersion in 2% TPGS/1.5% HPMCAS-HF/1.5% PVP-VA with 50 mM citrate pH 5.

Example 17. Compound 1 in Mouse CIA Model

Compound 1 was tested in the therapeutic mouse collagen-induced arthritis (CIA) model at 2.5 mg/kg BID (5 mg/kg/day), 5 mg/kg BID (10 mg/kg/day) or 10 mg/kg BID (20 mg/kg/day). Fostamatinib, a Syk small molecule inhibitor used as a reference standard, was dosed orally at 30 mg/kg BID (60 mg/kg/day). Compounds were dosed for 10 days in a 12/12-hour BID dosing regimen until the end of the study. Compound 1 was formulated in 0.2% MC, 1% SLS. Dosing volume was 10 mL/kg. Terminal plasma samples were collected at 2, 4 and 12 hours post last dose. All four paws and both knees were collected and processed for histopathology.

Figure 1:
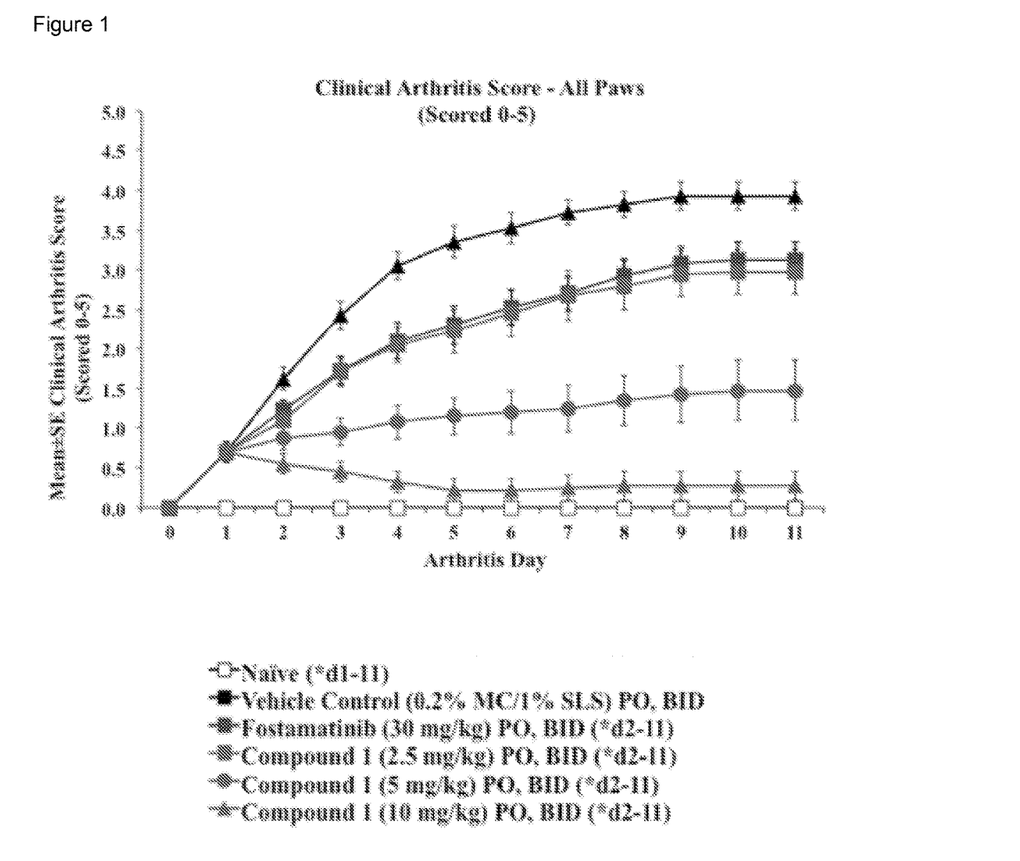
FIG. 1 shows the results for Compound 1 tested in the therapeutic mouse collagen-induced arthritis (CIA) model at 2.5 mg/kg BID, 5 mg/kg BID, and 10 mg/kg BID (20 mg/kg/day).
Figure 2:
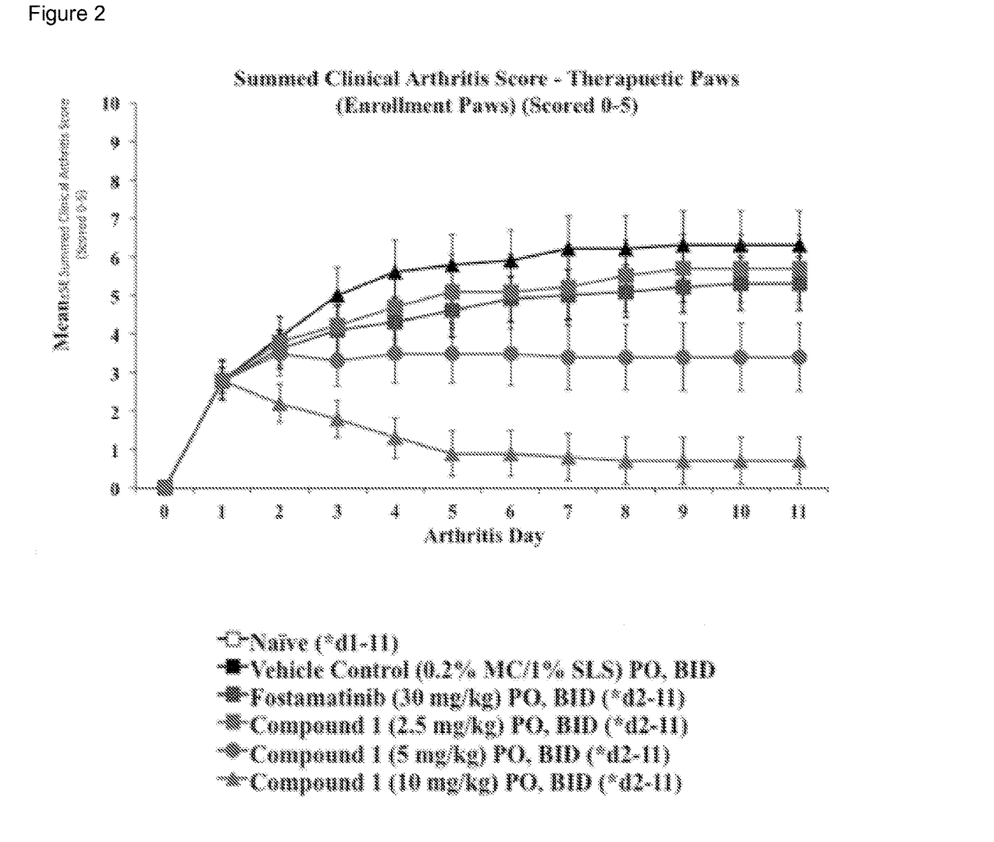
FIG. 2 shows the results for Compound 1 tested in the CIA model at 2.5 mg/kg BID, 5 mg/kg BID, and 10 mg/kg BID (20 mg/kg/day). The results are shown only for those paws showing clinical signs of arthritis at enrollment
Figure 3:
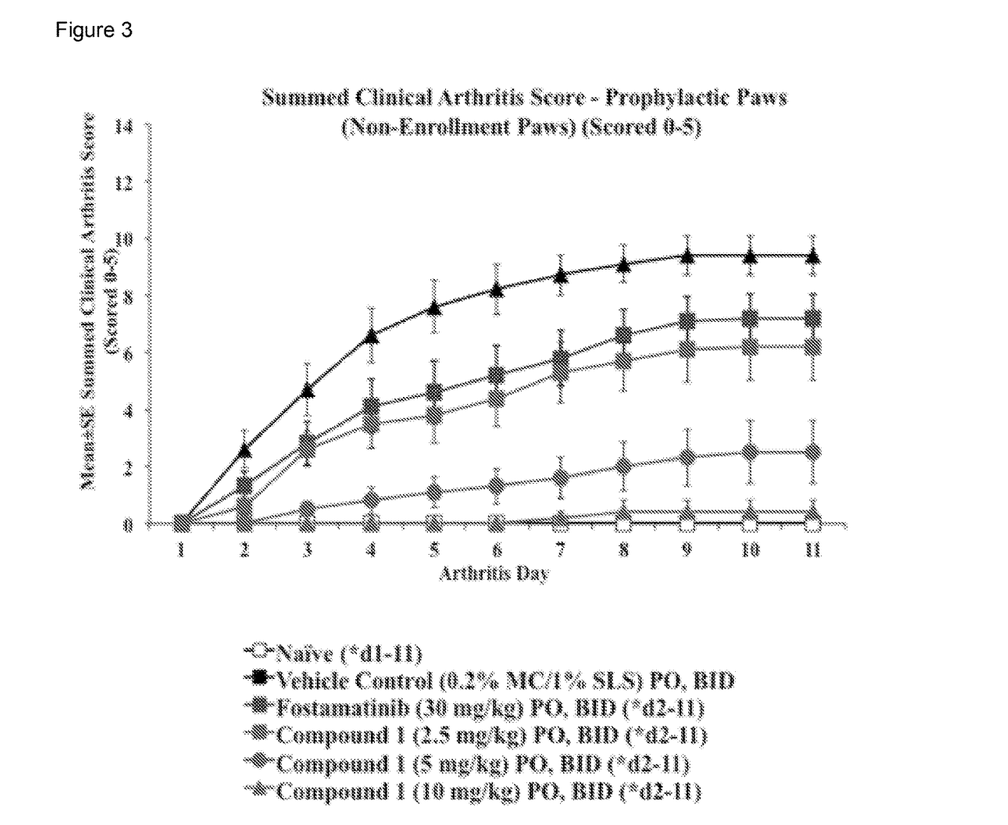
FIG. 3 shows the results for Compound 1 tested in the CIA model at 2.5 mg/kg BID, 5 mg/kg BID, and 10 mg/kg BID (20 mg/kg/day). The results are shown only for those paws showing no clinical signs of arthritis at enrollment.

Treatment with Compound 1 showed significant beneficial effect in the CIA model as determined by evaluation of clinical arthritis scores and histopathology of the joints. Arthritis scores measured daily were significantly reduced toward normal for mice treated with 2.5 mg/kg BID Compound 1 (*d2-11), 5 mg/kg BID Compound 1 (*d2-11), 10 mg/kg BID Compound 1 (*d2-11), or 30 mg/kg BID Fostamatinib (*d2-11) as compared to vehicle controls. See FIG. 1. When considering only those paws showing clinical signs of arthritis at enrollment (therapeutic paws), clinical arthritis scores were significantly reduced for mice treated with 5 mg/kg BID Compound 1 (*d5-11) or 10 mg/kg BID Compound 1 (*d2-11), but not for the 30 mg/kg BID Fostamatinib treatment groups. See FIG. 2. When considering only those paws showing no clinical signs of arthritis at enrollment (prophylactic paws), clinical arthritis scores were significantly reduced for mice treated with 2.5 mg/kg BID Compound 1 (*d2, 4-11), 5 mg/kg Compound 1 BID (*d2-11), 10 mg/kg Compound 1 BID (*d2-11) or 30 mg/kg BID Fostamatinib (*d5-9) as compared to vehicle controls. See FIG. 3.

Figure 4:
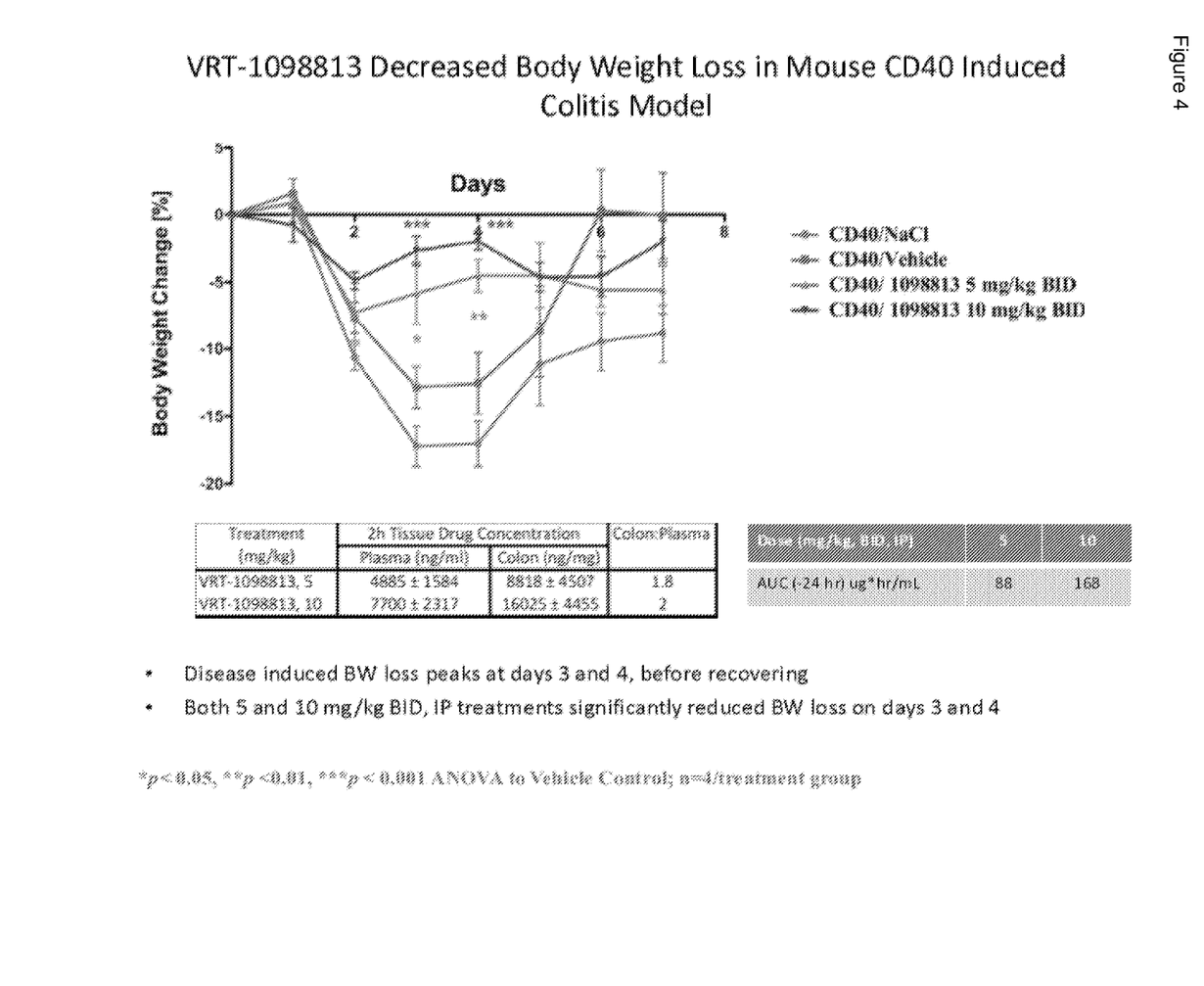
FIG. 4 shows the results for Compound 1 tested in the IBD model at 5 mg/kg BID and 10 mg/kg BID.

As shown in Table 13, clinical arthritis scores expressed as area under the curve (AUC) were significantly reduced toward normal for mice treated with 30 mg/kg BID Fostamatinib (25%), 2.5 mg/kg BID Compound 1 (28%), 5 mg/kg BID Compound 1 (63%) or 10 mg/kg BID Compound 1 (89%) as compared to vehicle controls. When considering therapeutic paws only, arthritis scores AUC were significantly reduced for mice treated with 10 mg/kg BID Compound 1 (79%). When considering prophylactic paws only, arthritis scores AUC were significantly reduced for mice treated with 30 mg/kg BID Fostamatinib (32%), 2.5 mg/kg BID Compound 1 (42%), 5 mg/kg BID Compound 1 (81%) and 10 mg/kg BID Compound 1 (98%) as compared to vehicle controls.

treated with Compound 1 at 5 mg/kg b.i.d. (*p<0.05 d3, p<0.01 d4) or 10 mg/kg b.i.d. (*p<0.001 d3-4) as compared to vehicle controls.

TABLE 13

Clinical arthritis scores for Compound 1 in CIA model

| | Clinical Score Data | | | Histopathology Summed Score | | |
| --- | --- | --- | --- | --- | --- | --- |
| Treatment (mg/kg BID) | All Paw Score AUC (SEM) | Therapeutic Paw Score AUC (SEM) | Prophylactic Paw Score AUC (SEM) | Six Joints (SEM) | Paws (SEM) | Knees (SEM) |
| Naive | *0 (SE 0.00) | | *0 (0.00) | *0 (0.00) | *0 (0.00) | *0 (0.00) |
| Vehicle control (0.2% MC/1% SLS) | 31.69 (1.42) | 55.75 (7.5) | 71.00 (6.96) | 11.3 (0.69) | 12.69 (0.46) | 8.63 (1.51) |
| Fostamatinib, 30 | *23.61 (1.84) | 46.15 (6.04) | *48.30 (7.71) | 9.80 (8.0) | 10.25 (0.94) | 8.90 (0.97) |
| Compound 1, 2.5 | *22.76 (2.33) | 49.25 (8.51) | *41.35 (8.37) | 7.70 (1.03) | 8.14 (1.05) | 6.83 (1.19) |
| Compound 1, 5 | *11.84 (2.48) | 34.00 (7.59) | *13.35 (6.03) | *3.27 (0.88) | *3.64 (1.08) | *2.53 (0.74) |
| Compound 1, 10 | *3.34 (1.42) | *11.75 (5.47) | *1.60 (1.60) | *0.75 (0.42) | *0.79 (0.50) | *0.68 (0.57) |

*p < 0.05 ANOVA or Kruskal-Wallis test to Vehicle

Example 18. Compound 1 in Mouse IBD Model

The PI3Kγ inhibitor, Compound 1, was tested in a CD40 induced colitis model to determine its effect on disease course. The CD40 model of IBD is induced by injecting an anti-CD40 monoclonal antibody (agonist, i.e., activating antibody versus neutralizing antibody) into T and B cell deficient mice (Rag 1–/– mice) to induce both systemic and intestinal inflammation that leads to colitis and wasting disease via the innate immune pathway. (See, e.g., Immunity 25, 309-318, August 2006). Briefly, Rag1 knock-out mice were injected IP with the anti-CD40 monoclonal antibody FGK45. Starting on Day 0, mice were treated with PBS, vehicle or Compound 1 at 5 mg/kg b.i.d. or 10 mg/kg b.i.d. Compound 1 was administered IP for 7 days on a 10/14-hour b.i.d. dosing regimen. Compound 1 was formulated in 5% NMP/15% PEG-400/80% in a 0.5% HPMC-E50 solution in water. At study termination, serum and colon samples were collected at 2 hours following the last dose for drug concentration analysis. Body weights were measured daily during the study. Compound 1 concentrations were analyzed in the plasma samples collected 2 hours following the final dose at study termination. Concentrations were determined using a high performance liquid chromatography/tandem mass spectrometry (HPLC/MS/MS) method.

Mice injected with anti-CD40 monoclonal antibody and treated with vehicle or PBS had body weight loss (measured as percent change from baseline) that began on day 1 and peaked at day 3-4 before recovering towards baseline. As shown in FIG. 4, disease-induced body weight loss was 17.2% and 17% on days 3 and 4, respectively, in the PBS treated group and 12.8% and 12.6% on days 3 and 4, respectively, in the vehicle treated group. FIG. 4 also shows that body weight loss was significantly inhibited in mice

TABLE 14

Tissue Concentrations of Compound 1 in the CD40-induced IBD Model

| | 2 h Tissue Drug Concentration | | |
| --- | --- | --- | --- |
| Treatment, mg/kg b.i.d. | Plasma (ng/mL) | Colon (ng/mg) | Colon:Plasma |
| Compound 1, 5 | 4020 ± 4520 | 6110 ± 6350 | 1.5 |
| Compound 1, 10 | 6220 ± 6190 | 7480 ± 9700 | 1.2 |

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

or a pharmaceutically acceptable salt thereof.

2. A pharmaceutical composition comprising the compound according to claim 1 and a pharmaceutically acceptable carrier, adjuvant, or vehicle.

3. A method of treating or lessening the severity of a disease or condition selected from an autoimmune disease or an inflammatory disease selected from rheumatoid arthritis, inflammatory bowel disease, ulcerative colitis, and Crohns' disease, comprising the step of administering to said patient the compound or salt thereof according to claim 1, or a pharmaceutical composition thereof.

4. The method according to claim 3, wherein said disease or disorder is rheumatoid arthritis.

5. A method of inhibiting PI3K-gamma kinase activity in a biological sample comprising contacting said biological sample with the compound according to claim 1, or a composition comprising said compound.

6. A method of selectively inhibiting a PI3K-gamma isoform over at least one other PI3K isoform comprising contacting a biological sample with or administering to a patient in need thereof a compound according to claim 1 or a composition comprising said compound.

7. The method according to claim 6, wherein the at least one other PI3K isoform is selected from the group consisting of PI3K-alpha, PI3K-beta, PI3K-delta and combinations thereof.

* * * * *